(12) United States Patent
Liu

(10) Patent No.: US 11,013,272 B2
(45) Date of Patent: May 25, 2021

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 292 days.

(21) Appl. No.: 16/368,906

(22) Filed: Mar. 29, 2019

(65) Prior Publication Data

US 2020/0214359 A1 Jul. 9, 2020

(30) Foreign Application Priority Data

Jan. 5, 2019 (CN) .......................... 201910009622.3
Jan. 5, 2019 (CN) .......................... 201920031778.7

(51) Int. Cl.
*A24F 13/00* (2006.01)
*A24F 47/00* (2020.01)
*A24F 7/00* (2006.01)
*H01M 50/213* (2021.01)

(52) U.S. Cl.
CPC .............. *A24F 47/008* (2013.01); *A24F 7/00* (2013.01); *H01M 50/213* (2021.01); *H01M 2220/30* (2013.01)

(58) Field of Classification Search
CPC ...................................................... A24F 47/00

USPC .................................................. 131/328–329
See application file for complete search history.

(56) References Cited

U.S. PATENT DOCUMENTS

| 4,922,901 A * | 5/1990 | Brooks | A24F 47/008 |
| | | | 128/203.26 |
| 9,949,512 B2 * | 4/2018 | Liu | A24F 40/40 |

* cited by examiner

*Primary Examiner* — Phuong K Dinh
(74) *Attorney, Agent, or Firm* — Matthias Scholl P.C.; Matthias Scholl

(57) ABSTRACT

An electronic cigarette, including an atomizing assembly, a battery assembly, and a box assembly. The atomizing assembly is disposed on the battery assembly. The atomizing assembly includes an e-liquid storage unit and an atomization unit. The atomizing assembly and the battery assembly are disposed in the box assembly. The e-liquid storage unit includes a mouthpiece, a seal ring adapted to seal the mouthpiece, a thread ring, a seal plug, an e-liquid tank, and a tank cover. The atomization unit includes an O-ring, a limit cover, an e-liquid conductive cotton, a heating wire, an insulation ring, and a joint. The battery assembly includes a seal, a support, a first battery cell, a base plate, a first magnet, a cartridge, and a battery cover. The box assembly includes an outer sliding cover, a first screw, an inner sliding cover, a second magnet, a fixed part, a flexible circuit board.

1 Claim, 6 Drawing Sheets

ELECTRONIC CIGARETTE

CROSS-REFERENCE TO RELATED APPLICATIONS

Pursuant to 35 U.S.C.§ 119 and the Paris Convention Treaty, this application claims foreign priority to Chinese Patent Application No. 201910009622.3 filed Jan. 5, 2019, and to Chinese Patent Application No. 201920031778.7 filed Jan. 5, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

This disclosure relates to an electronic cigarette.

Electronic cigarettes atomize nicotine-containing e-liquid.

Conventionally, the atomizing assembly fixedly communicates with the battery assembly. This may lead to leakage of the e-liquid. In addition, conventional electronic cigarettes must be charged between uses which negatively affects usability.

SUMMARY

The disclosure provides an electronic cigarette that can be charged when in use.

Provided is an electronic cigarette, comprising an atomizing assembly, a battery assembly, and a box assembly. The atomizing assembly is disposed on the battery assembly.

The atomizing assembly comprises an e-liquid storage unit and an atomization unit. The atomizing assembly and the battery assembly are disposed in the box assembly.

The e-liquid storage unit comprises a mouthpiece, a seal ring adapted to seal the mouthpiece, a thread ring, a seal plug, an e-liquid tank, and a tank cover; the atomization unit comprises an O-ring, a limit cover, an e-liquid conductive cotton, a heating wire, an insulation ring, and a joint.

The battery assembly comprises a seal, a support, a first battery cell, a base plate, a first magnet, a cartridge, and a battery cover.

The box assembly comprises an outer sliding cover, a first screw, an inner sliding cover, a second magnet, a fixed part, a flexible circuit board, a movable sleeve, a fixed pin, a compression spring, a switch, a guide strip, an upper transparent cover, a lower housing, a rectangular guide strip, a power button, a lower transparent cover, a foam cotton, a control board, a second battery cell, a second screw, an upper housing, and a housing.

The atomization unit is disposed in the e-liquid storage unit and is fixed by the tank cover; the seal plug is disposed on an upper part of the e-liquid tank and the tank cover is disposed on a lower part of the e-liquid tank; the thread ring is screwed on the e-liquid tank; the seal ring is disposed on the mouthpiece; the mouthpiece is inserted in a central hole of the e-liquid tank.

The O-ring is sheathed on the limit cover; the e-liquid conductive cotton wraps the heating wire; the heating wire is disposed in the limit cover; the insulation ring is sheathed on the joint; the joint is disposed on one end of the limit cover; the base plate comprises positive and negative electrodes connected to positive and negative electrodes of the first battery cell; the base plate and the first battery cell are disposed in the support; the seal is disposed on an upper part of the support, and the first magnet is disposed on a lower part of the support; the support is disposed on the cartridge; the battery cover is disposed on one end of the cartridge opposite to the seal; the e-liquid tank of the atomization unit is rotatably disposed in the cartridge.

The second magnet and the flexible circuit board are disposed on the fixed part; the inner sliding cover comprises a fixed groove and two side holes; the fixed part is disposed in the fixed groove of the inner sliding cover, and the compression spring is disposed in the two side holes of the inner sliding cover; the outer sliding cover is disposed on the inner sliding cover and is fixed by the first screw; the rectangular guide strip is attached to the lower housing; the movable sleeve is fixed on two fixed supports of the lower housing via the second screw; the switch is disposed in a fixed groove of the lower housing; the fixed pin is disposed in the movable sleeve; the power button is mounted at the bottom of the lower housing, the second battery cell is bonded to the control board, the foamed cotton is bonded to the second battery cell, and the control board is mounted to the lower housing and fixed by the second screw; the compression spring in the inner sliding cover is sheathed on the fixed pin of the lower housing; the inner sliding cover comprises a buckle fastened to the switch of the lower housing; the guide strip is attached to a sliding rail of the upper housing; the upper housing is disposed on the lower housing and fixed by the second screw; the upper transparent cover and the lower transparent cover are disposed at two ends of the lower housing, respectively; and the housing is fixed on the upper housing and the lower housing.

The box assembly can be opened and closed by pressing the outer sliding cover. When the outer sliding cover is pressed, under the action of external force, the compression spring will be deformed, so that the pin on the inner sliding cover moves inward to butt against the switch in the lower housing. As a result, the fastener on the switch is closed to lock the pin on the inner sliding cover, thus closing the box assembly. When the outer sliding cover is pressed again, the fastener on the switch in the lower housing is opened, and the outer sliding cover is ejected under the action of the compression spring, thus opening the box assembly. It is convenient to take out the e-cigarette for use and charge the e-cigarette in the box. The main body of the e-cigarette is located in the inner sliding cover. The electrical contacts on the flexible circuit board contact the positive and negative electrodes of the base plate of the battery assembly. A press of the power button starts the charging of the e-cigarette. Continuously pressing the power button for several times, for example, five times, can terminate the charging. The e-cigarette is suitable for use outdoors.

Advantages of the electronic cigarette according to embodiments of the disclosure are summarized as follows. The e-cigarette can be charged when in use. The atomizing assembly is detachably connected to the battery assembly. When not in use, the atomization unit is separated from the e-liquid storage unit. When the atomizing assembly is mounted on the battery assembly, the battery assembly will push the limit cover of the atomizing assembly to move towards the e-liquid tank, so that the e-liquid inlet of the limit cover enters the e-liquid tank to obtain the e-liquid. As a result, the leakage of the e-liquid is prevented when the e-cigarette is not in use.

DETAILED DESCRIPTION

To further illustrate, embodiments detailing an electronic cigarette are described below. It should be noted that the following embodiments are intended to describe and not to limit the disclosure.

Figure 1:
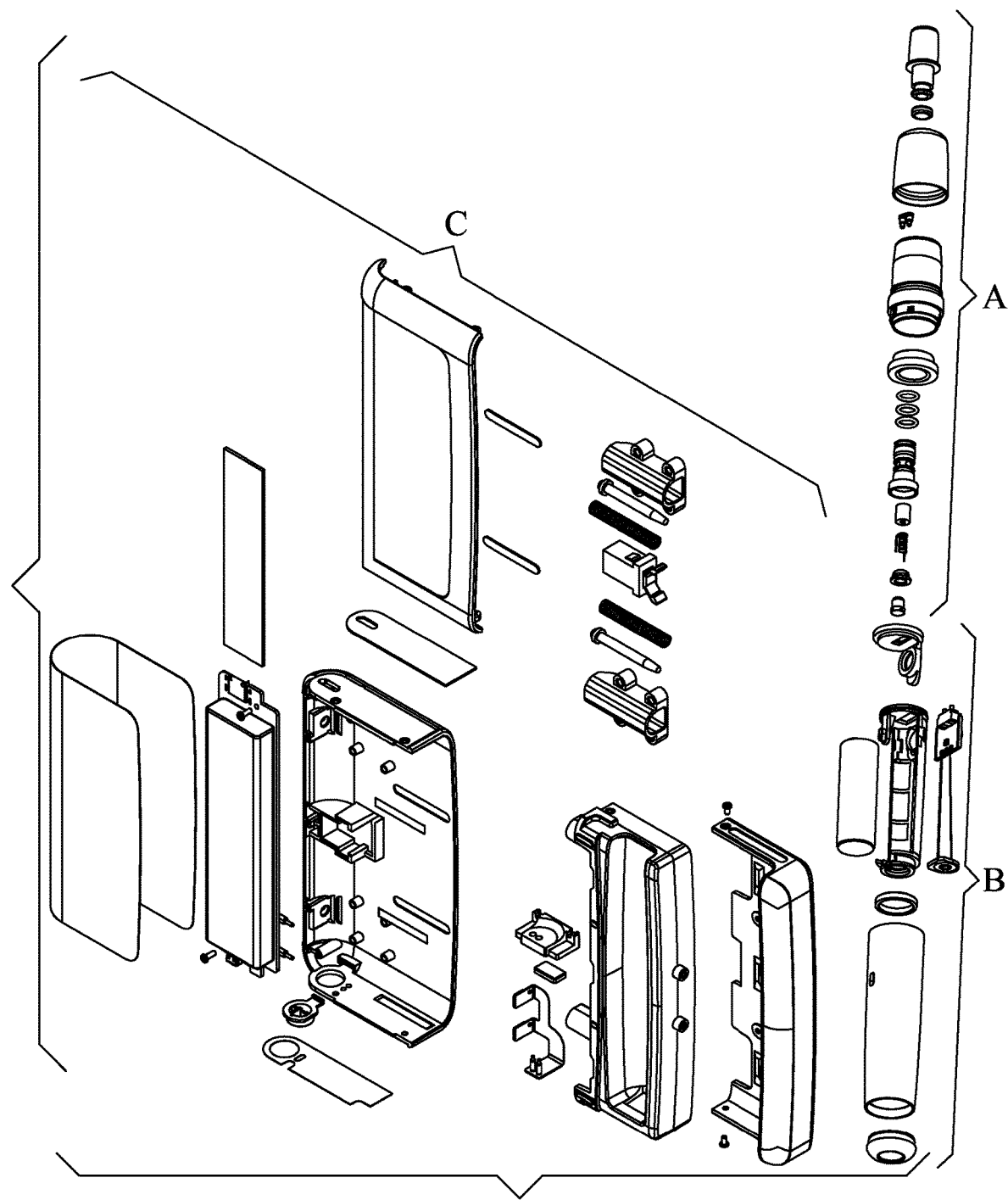
FIG. 1 is an exploded view of an electronic cigarette as described in the disclosure.
Figure 2:
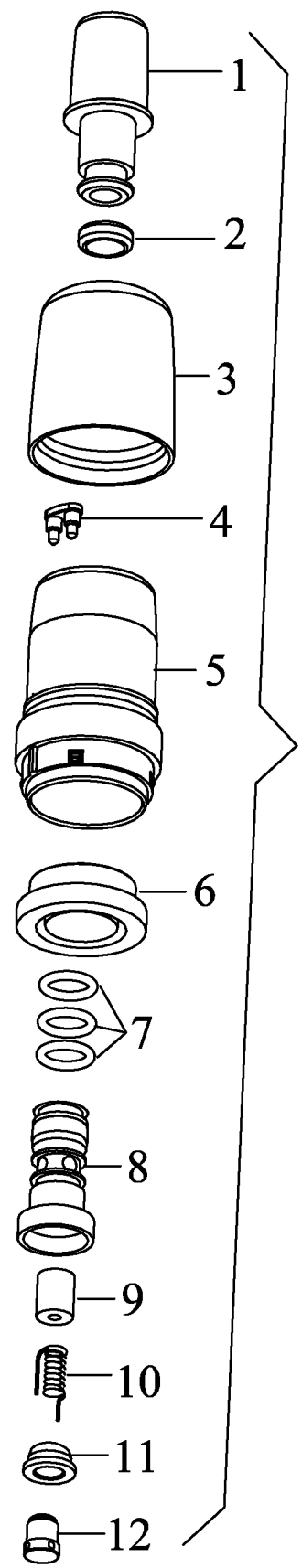
FIG. 2 is an exploded view of an atomizing assembly of an electronic cigarette as described in the disclosure.
Figure 3:
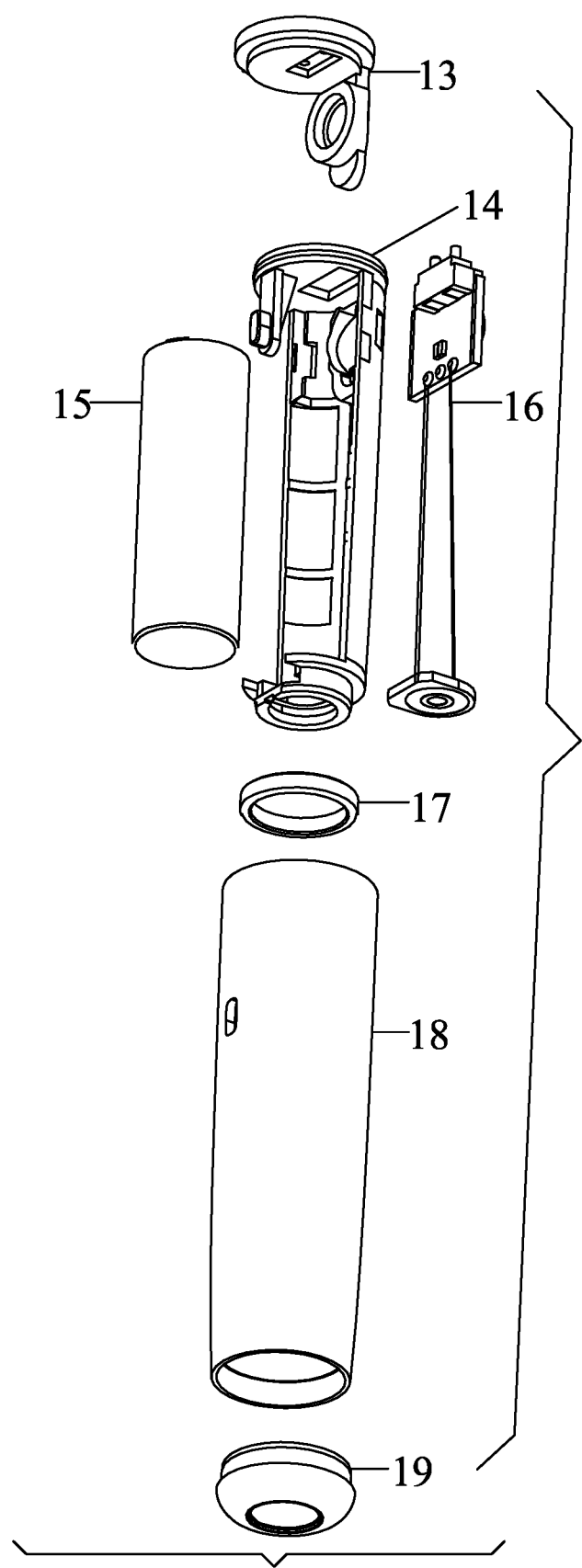
FIG. 3 is an exploded view of a battery assembly of an electronic cigarette as described in the disclosure.
Figure 4:
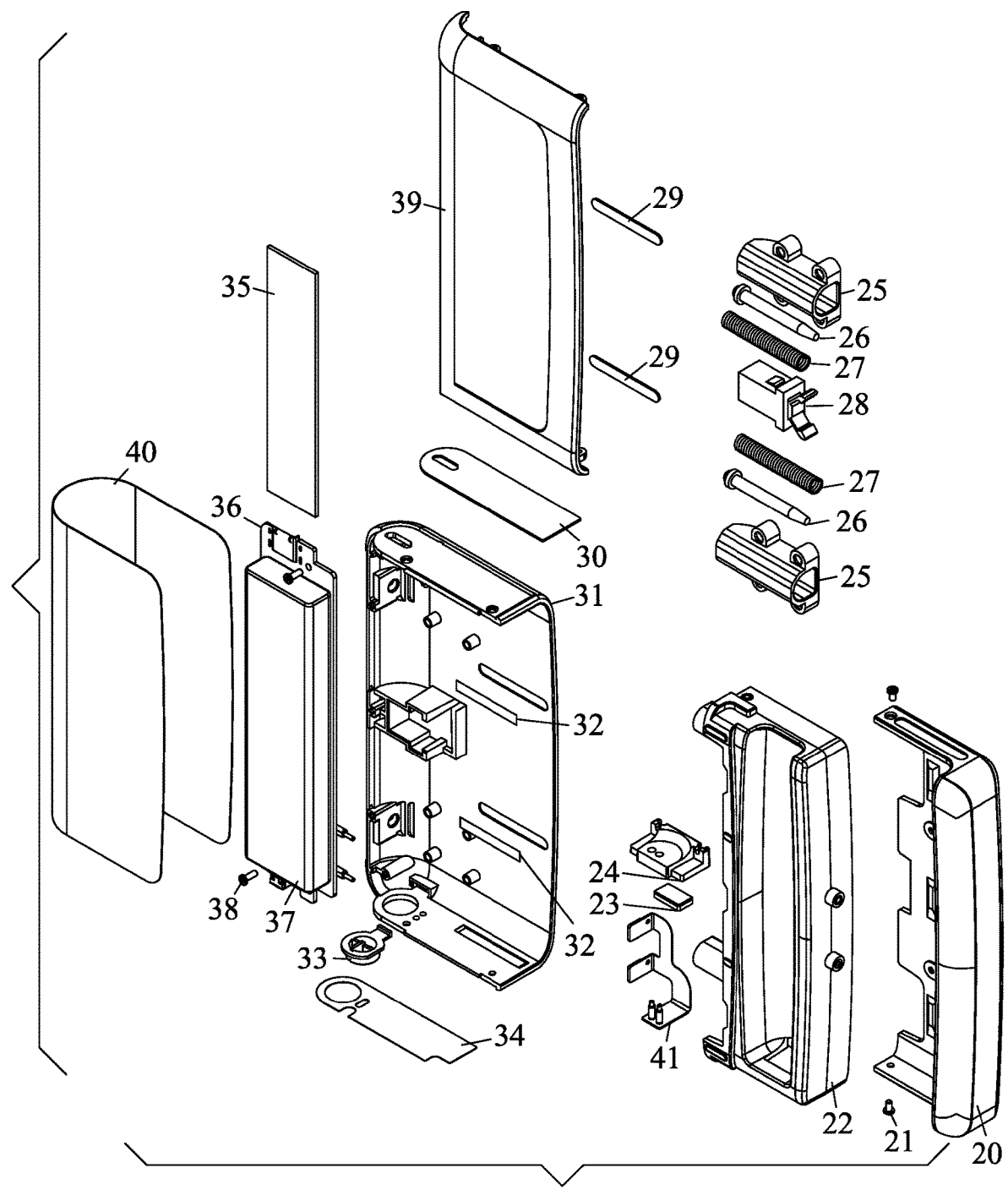
FIG. 4 is an exploded view of a box assembly of an electronic cigarette as described in the disclosure.
Figure 5:
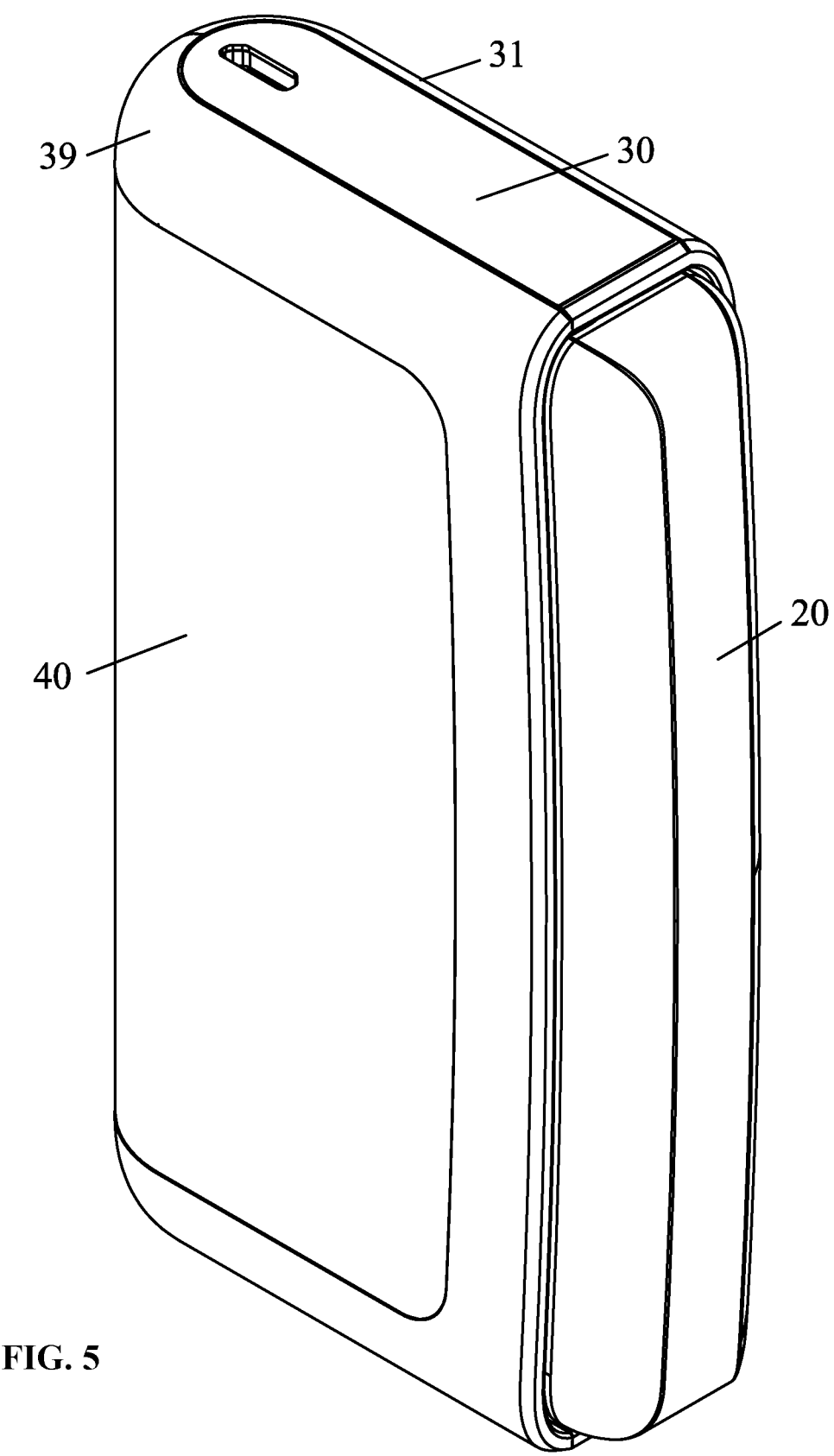
FIG. 5 is a stereogram of an electronic cigarette as described in the disclosure.
Figure 6:
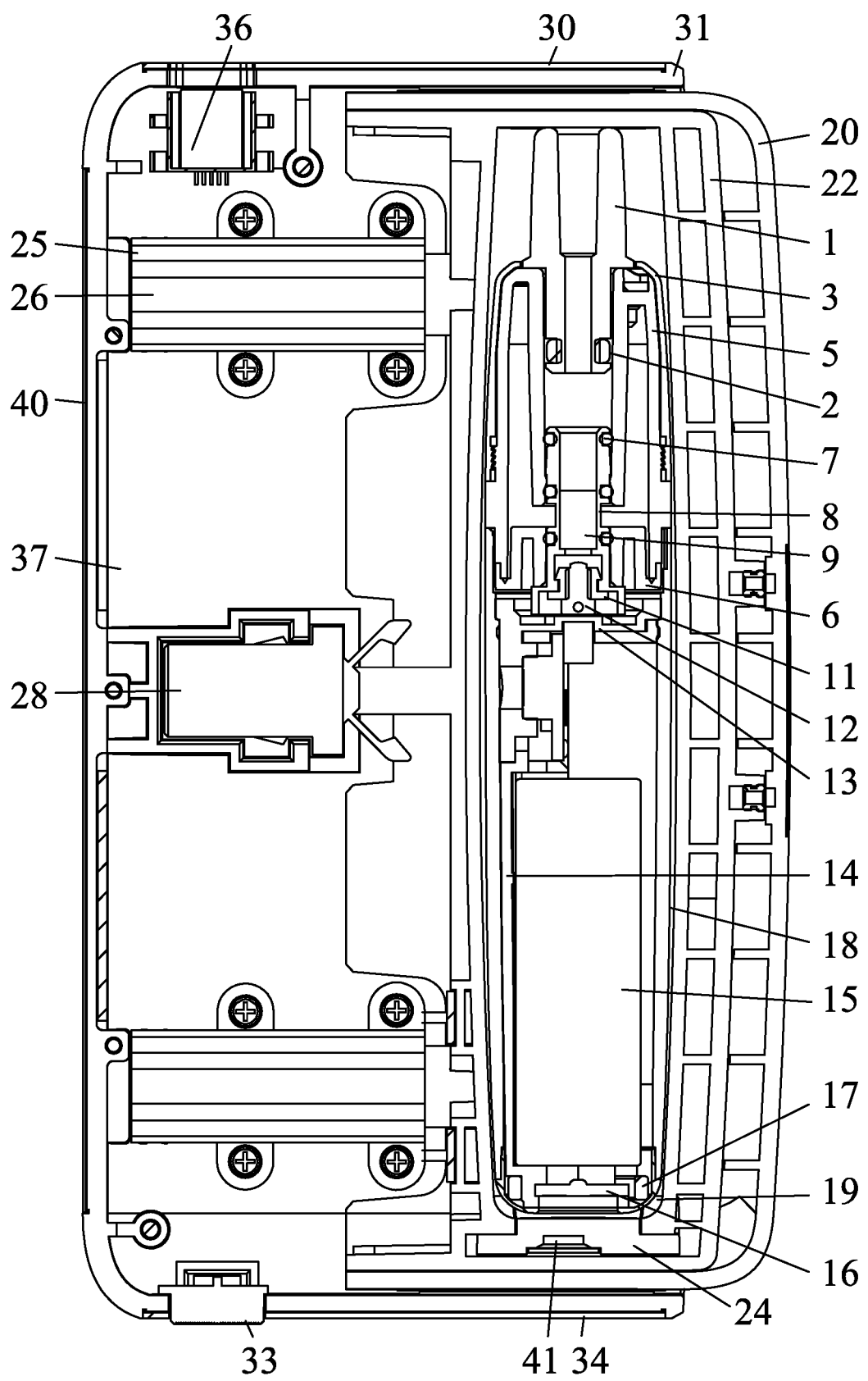
FIG. 6 is a sectional view of an electronic cigarette as described in the disclosure.

As shown in FIGS. 1-6, provided is an electronic cigarette, comprising: an atomizing assembly A; a battery assembly B, and a box assembly C. The atomizing assembly A is rotatably disposed on the battery assembly B. The atomizing assembly and the battery assembly are disposed in the box assembly C.

The atomizing assembly A comprises an e-liquid storage unit and an atomization unit; the e-liquid storage unit comprises a mouthpiece 1, a seal ring 2 adapted to seal the mouthpiece, a thread ring 3, a seal plug 4, an e-liquid tank 5, and a tank cover 6; the atomization unit comprises an O-ring 7, a limit cover 8, an e-liquid conductive cotton 9, a heating wire 10, an insulation ring 11, and a joint 12; the atomization unit is disposed in the e-liquid storage unit and is fixed by the tank cover 6; the seal plug 4 is disposed on an upper part of the e-liquid tank 5 and the tank cover 6 is disposed on a lower part of the e-liquid tank 5; the thread ring 3 is screwed on the e-liquid tank 5; the seal ring 2 is disposed on the mouthpiece 1; the mouthpiece 1 is inserted in a central hole of the e-liquid tank 5; the O-ring 7 is sheathed on the limit cover 8; the e-liquid conductive cotton 9 wraps the heating wire 10; the heating wire 10 is disposed in the limit cover 8; the insulation ring 11 is sheathed on the joint 12; the joint 12 is disposed on one end of the limit cover 8.

The battery assembly comprises a seal 13, a support 14, a first battery cell 15, a base plate 16, a first magnet 17, a cartridge 18, and a battery cover 19. The base plate 16 comprises positive and negative electrodes connected to positive and negative electrodes of the first battery cell 15; the base plate 16 and the first battery cell 15 are disposed in the support 14; the seal 13 is disposed on an upper part of the support 14, and the first magnet 17 is disposed on a lower part of the support 14; the support 14 is disposed on the cartridge 18; the battery cover 19 is disposed on one end of the cartridge 18 opposite to the seal 13; the e-liquid tank 5 of the atomization unit is rotatably disposed in the cartridge 18.

When the atomizing assembly and the battery assembly are not combined, the e-liquid storage unit and the atomization unit of the atomizing assembly are separated from each other. The e-liquid inlet of the limit cover 8 is sealed in the tank cover 6, so that the e-liquid cannot enter the e-liquid conductive cotton 9. When the atomizing assembly and the battery assembly are combined, under the action of external force, the battery assembly will push the limit cover 8 of the atomizing assembly to move towards the e-liquid tank 5. The e-liquid inlet of the limit cover 8 moves from the tank cover 6 to the e-liquid tank 5. The design can effectively prevent the leakage of the e-liquid.

The box assembly C comprises an outer sliding cover 20, a first screw 21, an inner sliding cover 22, a second magnet 23, a fixed part 24, a flexible circuit board 41, a movable sleeve 25, a fixed pin 26, a compression spring 27, a switch 28, a guide strip 29, an upper transparent cover 30, a lower housing 31, a rectangular guide strip 32, a power button 33, a lower transparent cover 34, a foam cotton 35, a control board 36, a second battery cell 37, a second screw 38, an upper housing 39, and a housing 40. The second magnet 23 and the flexible circuit board 41 are disposed on the fixed part 24; the inner sliding cover 22 comprises a fixed groove and two side holes; the fixed part 24 is disposed in the fixed groove of the inner sliding cover 22, and the compression spring 27 is disposed in the two side holes of the inner sliding cover 22; the outer sliding cover 20 is disposed on the inner sliding cover 22 and is fixed by the first screw; the rectangular guide strip 32 is attached to the lower housing 31; the movable sleeve 25 is fixed on two fixed supports of the lower housing 31 via the second screw 38; the switch 28 is disposed in a fixed groove of the lower housing 31; the fixed pin 26 is disposed in the movable sleeve 25; the power button 33 is mounted at the bottom of the lower housing 31, the second battery cell 37 is bonded to the control board 36, the foamed cotton 35 is bonded to the second battery cell 37, and the control board 36 is mounted to the lower housing 31 and fixed by the second screw 38; the compression spring 27 in the inner sliding cover 22 is sheathed on the fixed pin 26 of the lower housing 31; the inner sliding cover 22 comprises a buckle fastened to the switch 28 of the lower housing 31; the guide strip 29 is attached to a sliding rail of the upper housing 39; the upper housing 39 is disposed on the lower housing 31 and fixed by the second screw 38; the upper transparent cover 30 and the lower transparent cover 34 are disposed at two ends of the lower housing 31, respectively; and the housing 40 is fixed on the upper housing 39 and the lower housing 31.

The box assembly can be opened and closed by pressing the outer sliding cover 20. When the outer sliding cover 20 is pressed, under the action of external force, the compression spring 27 will be deformed, so that the pin on the inner sliding cover 22 moves inward to butt against the switch 28 in the lower housing 31. As a result, the fastener on the switch 28 is closed to lock the pin on the inner sliding cover 22, thus closing the box assembly. When the outer sliding cover 20 is pressed again, the fastener on the switch 28 in the lower housing 31 is opened, and the outer sliding cover 20 is ejected under the action of the compression spring 27, thus opening the box assembly. This is convenient to take out the e-cigarette for use and charge the e-cigarette in the box. The main body of the e-cigarette is located in the inner sliding cover 22. The electrical contacts on the flexible circuit board 41 contact the positive and negative electrodes of the base plate 16 of the battery assembly. Press the power button 33 to start the charging of the e-cigarette. Continuously pressing the power button 33 for several times can terminate the charging. The e-cigarette capable of being charged is suitable for use outdoors.

It will be obvious to those skilled in the art that changes and modifications may be made, and therefore, the aim in the appended claims is to cover all such changes and modifications.

What is claimed is:

1. An electronic cigarette, comprising:
   an atomizing assembly, the atomizing assembly comprising an e-liquid storage unit and an atomization unit; the e-liquid storage unit comprising a mouthpiece, a seal ring adapted to seal the mouthpiece, a thread ring, a seal plug, an e-liquid tank, and a tank cover; the atomization unit comprising an O-ring, a limit cover, an e-liquid conductive cotton, a heating wire, an insulation ring, and a joint;

a battery assembly, the battery assembly comprising a seal, a support, a first battery cell, a base plate, a first magnet, a cartridge, and a battery cover; and a box assembly, the box assembly comprising an outer sliding cover, a first screw, an inner sliding cover, a second magnet, a fixed part, a flexible circuit board, a movable sleeve, a fixed pin, a compression spring, a switch, a guide strip, an upper transparent cover, a lower housing, a rectangular guide strip, a power button, a lower transparent cover, a foam cotton, a control board, a second battery cell, a second screw, an upper housing, and a housing;

wherein:

the atomizing assembly is rotatably disposed on the battery assembly;

the atomizing assembly and the battery assembly are disposed in the box assembly;

the atomization unit is disposed in the e-liquid storage unit and is fixed by the tank cover;

the seal plug is disposed on an upper part of the e-liquid tank and the tank cover is disposed on a lower part of the e-liquid tank; the thread ring is screwed on the e-liquid tank; the seal ring is disposed on the mouthpiece; the mouthpiece is inserted in a central hole of the e-liquid tank;

the O-ring is sheathed on the limit cover; the e-liquid conductive cotton wraps the heating wire; the heating wire is disposed in the limit cover; the insulation ring is sheathed on the joint; the joint is disposed on one end of the limit cover;

the base plate comprises positive and negative electrodes connected to positive and negative electrodes of the first battery cell; the base plate and the first battery cell are disposed in the support; the seal is disposed on an upper part of the support, and the first magnet is disposed on a lower part of the support; the support is disposed on the cartridge; the battery cover is disposed on one end of the cartridge opposite to the seal; the e-liquid tank of the atomization unit is rotatably disposed in the cartridge;

the second magnet and the flexible circuit board are disposed on the fixed part; the inner sliding cover comprises a fixed groove and two side holes; the fixed part is disposed in the fixed groove of the inner sliding cover, and the compression spring is disposed in the two side holes of the inner sliding cover; the outer sliding cover is disposed on the inner sliding cover and is fixed by the first screw; the rectangular guide strip is attached to the lower housing; the movable sleeve is fixed on two fixed supports of the lower housing via the second screw; the switch is disposed in a fixed groove of the lower housing; the fixed pin is disposed in the movable sleeve; the power button is mounted at the bottom of the lower housing, the second battery cell is bonded to the control board, the foamed cotton is bonded to the second battery cell, and the control board is mounted to the lower housing and fixed by the second screw; the compression spring in the inner sliding cover is sheathed on the fixed pin of the lower housing; the inner sliding cover comprises a buckle fastened to the switch of the lower housing; the guide strip is attached to a sliding rail of the upper housing; the upper housing is disposed on the lower housing and fixed by the second screw; the upper transparent cover and the lower transparent cover are disposed at two ends of the lower housing, respectively; and the housing is fixed on the upper housing and the lower housing.

* * * * *